United States Patent [19]
Johnson et al.

[11] 3,975,949
[45] Aug. 24, 1976

[54] LEAK DETECTOR PROBE FOR FUEL RODS

[75] Inventors: Keith O. Johnson, Kennewick; Fredrick M. Coffman, Richland, both of Wash.

[73] Assignee: Exxon Nuclear Company, Inc., Bellevue, Wash.

[22] Filed: Jan. 10, 1974

[21] Appl. No.: 432,290

[52] U.S. Cl............................. 73/71.5 R; 73/67.2; 176/19 LD; 176/80
[51] Int. Cl.² ................... G01N 29/00; G21C 17/06
[58] Field of Search............ 73/67.2, 69, 70, 71.5 R, 73/71.5 US, 67, 71.2, 71.4; 176/19 LD, 19 R, 80

[56] References Cited
UNITED STATES PATENTS

| | | | |
|---|---|---|---|
| 1,686,138 | 10/1928 | Marvel............................. | 73/71.4 X |
| 3,296,864 | 1/1967 | Kealy et al............................ | 73/339 |
| 3,387,604 | 6/1968 | Erikson.................... | 73/71.5 US UX |
| 3,638,053 | 1/1972 | Schenk et al....................... | 73/70 X |
| 3,641,811 | 2/1972 | Gnaedinger, Jr. et al. ....... | 73/71.5 X |
| 3,685,350 | 8/1972 | Pettinato........................ | 73/71.5 US |
| 3,762,496 | 10/1973 | Milberger et al. .................. | 73/70 X |
| 3,813,286 | 5/1974 | Goldman et al. .................. | 176/19 R |
| 3,823,068 | 7/1974 | Worlton et al........................ | 176/80 |

*Primary Examiner*—Richard C. Queisser
*Assistant Examiner*—John S. Appleman
*Attorney, Agent, or Firm*—Harold N. Wells; F. Donald Paris

[57] ABSTRACT

Nuclear reactor fuel rod leakage is determined by measurement of vibrational characteristics of a resilient, flexible means sealed within the upper end caps of the fuel elements. The flexible means, which is preferably a metallic diaphragm, is set into motion and the vibration measurements are made by a special tool which fits over the end cap of the fuel element to be tested.

16 Claims, 4 Drawing Figures

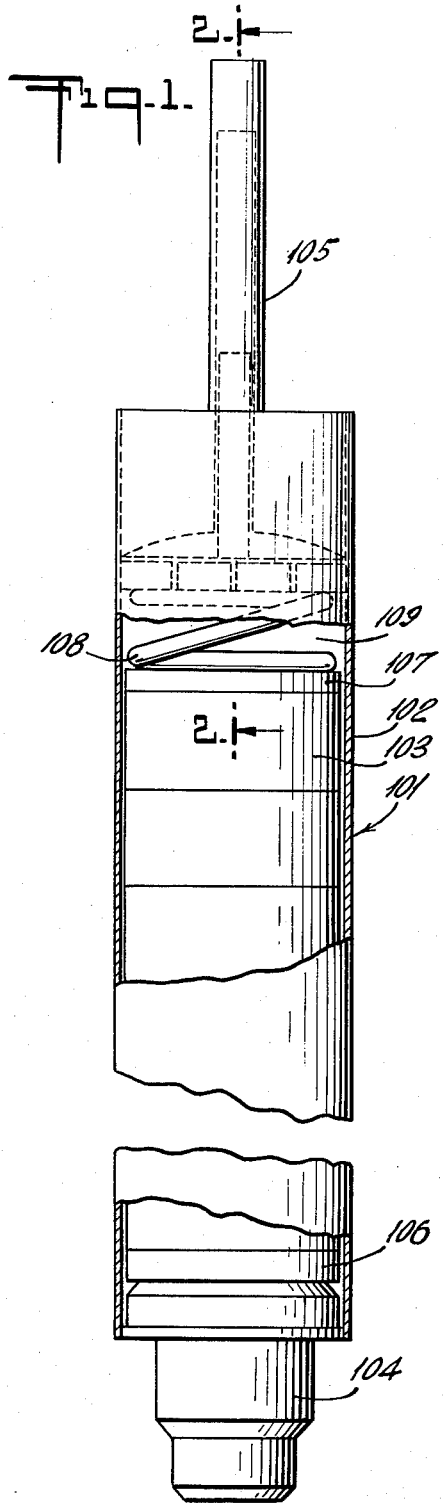
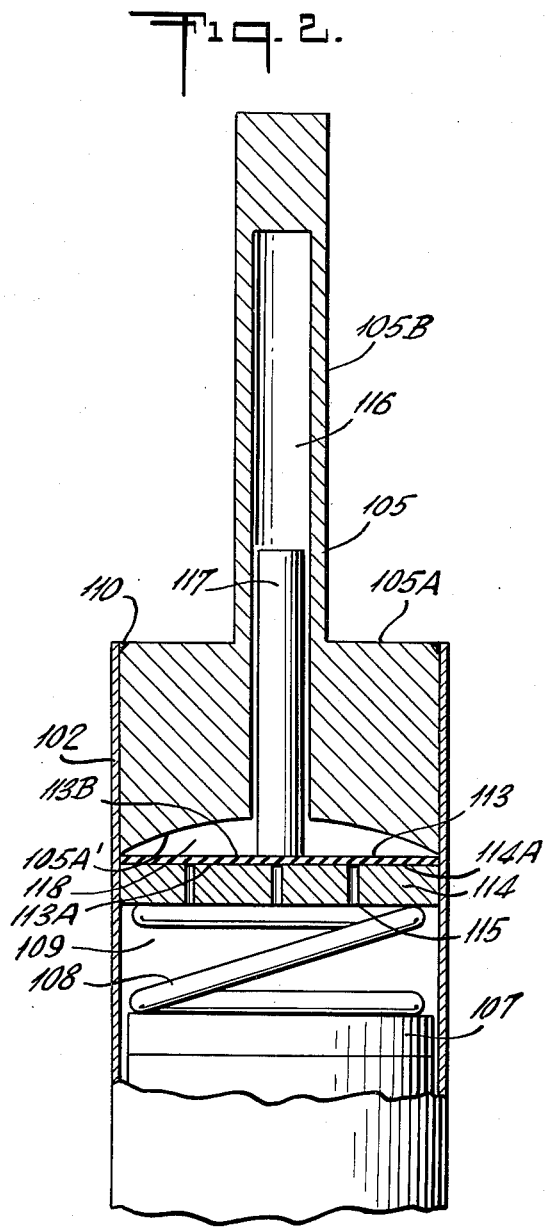

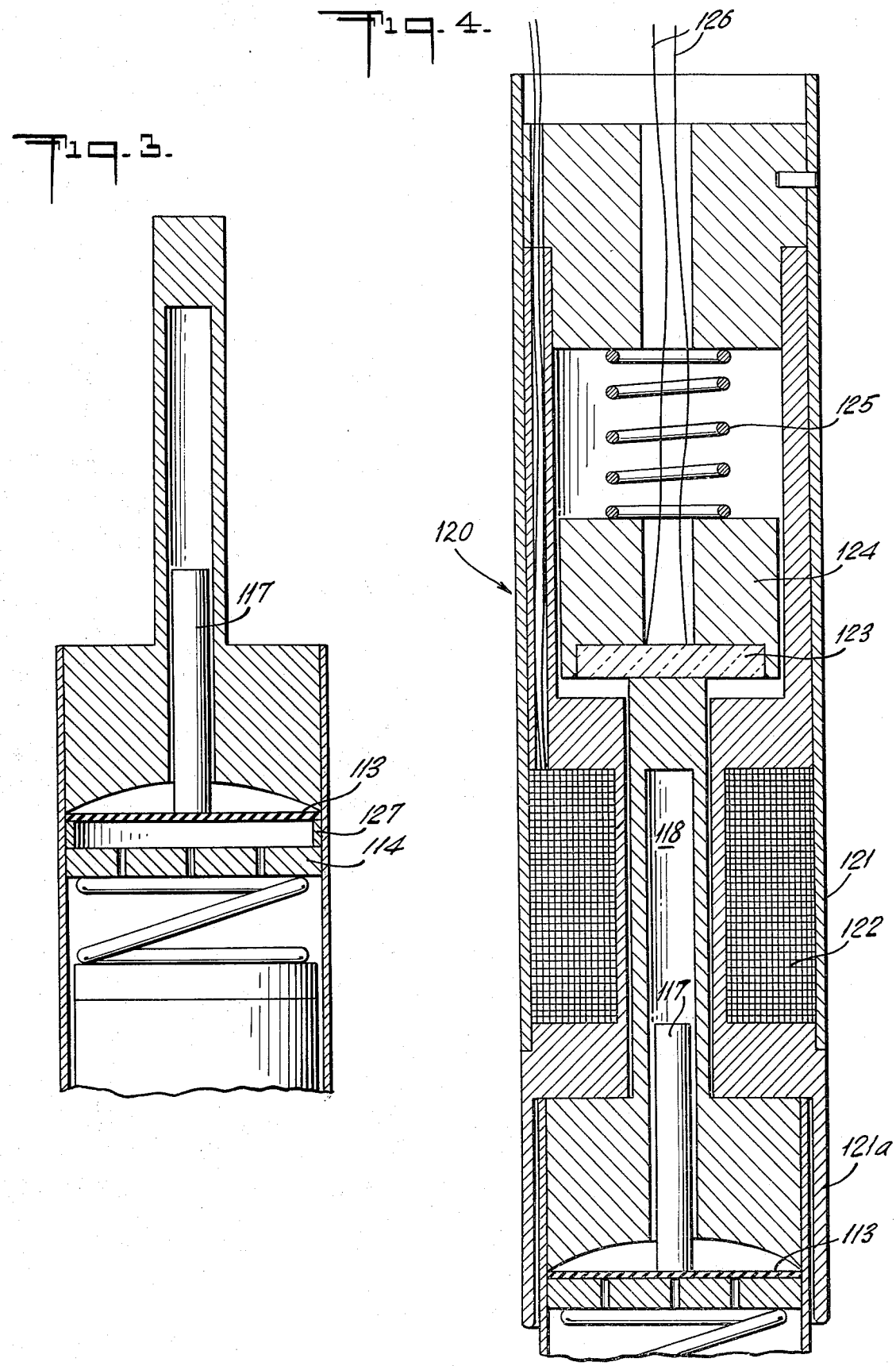

LEAK DETECTOR PROBE FOR FUEL RODS

CROSS-REFERENCE TO RELATED APPLICATIONS

This application is related to copending application U.S. Ser. No. 422,383, filed Dec. 6, 1973, which will be incorporated by reference.

BACKGROUND OF THE INVENTION

This invention relates to nuclear reactors and, in particular, to a method and apparatus for determining if a nuclear reactor fuel rod is leaking.

One problem faced in the utilization of nuclear power as an energy source is the radioactive contamination of the reactor facility. One source of such contamination is leakage of fission product gases and other radioactive materials from a fuel element during reactor operation. These contaminants then enter the coolant material and are carried to other areas in the reactor facility. When such contamination occurs, it is necessary that nuclear fuel bundles which have prematurely failed be removed from the reactor core and replaced with fresh fuel. The replacement process, normally accomplished during scheduled plant outages, involves two steps. First, fuel bundles suspected of containing defective fuel pins are identified, then they are removed and replaced with good fuel bundles. After removal, suspect bundles may be disassembled, the defective fuel rods segregated by nondestructive examination, and then reassembled with good fuel rods.

With present practice, identification of faulty fuel, either in-core or after bundle disassembly, is a time-consuming process which contributes substantially to the overall cost of reconstituting the fuel load.

Attempts have been made to reduce and overcome the disadvantages of the standard practice by devising various methods for rapidly testing the fuel rods for leakage without having to remove them from the reactor core; see U.S. Pat. Nos. 3,296,864, 3,230,771 and 3,350,271. These methods have not been successful because the methods could not accurately determine the leakage or the apparatus could not function in the reactor environment.

In copending application, Ser. No. 200,698, filed Nov. 22, 1971, now U.S. Pat. No. 3,823,068, a method to detect fuel pin leakage without removing the fuel elements from the reactor is disclosed wherein the fission gas pressure activates a flexible diaphragm or bellows assembly to produce measurable fluctuations in an eddy current established about the fuel rod upper end cap.

In copending application, Ser. No. 422,383, filed Dec. 6, 1973, another method and apparatus for facilitating the detection of fuel pin leakage and reducing downtime for nuclear reactors is disclosed. The instant invention comprises a probe for use with the apparatus of the copending application.

SUMMARY OF THE INVENTION

It has been found that fuel pin leakage can be rapidly determined by measuring the vibrational characteristics of a flexible means located in a specially constructed upper end cap assembly. This test may be done without removing the fuel bundles from the reactor or alternatively may be done after the suspected bundles have been removed.

The upper end cap assembly comprises a particularly designed upper end cap, a resilient means which is usually a metallic diaphragm and a disc having bleed holes. The upper end cap is designed so that its shoulder section fits into the upper portion of a fuel rod and it is sealed thereto. The shoulder section has a concave bottom surface and an axial cavity that extends from the concave surface into the adjoining shank section of the end cap. A resilient, flexible metal diaphragm is placed next to the bottom surface of the shoulder section, thus forming a cavity sealed from the remainder of the fuel rod. Adjacent the diaphragm and outside the sealed cavity is a perforated disc which permits pressure buildup in the fuel rod to be exerted against the diaphragm. Such pressure buildup will cause a movement of the diaphragm and such movement can be detected by measuring the vibrational characteristics of the diaphragm, which have found to vary depending on the pressure. The diaphragm is conveniently set into vibration by a metal rod positioned within the axial cavity of the end cap shank (within the sealed cavity). Preferably this is done by lifting the rod with an external magnetic field and releasing it. The kinetic energy of the rod is dissipated by its impacts with the diaphragm. The number and amplitude of the bounces can then be detected by an acoustic sensor placed on the external surface of the end cap shank section. In addition, the characteristic resonant frequencies of the diaphragm and the end cap may be measured. By examining the vibrational frequencies, it is possible to determine whether a normal pressure buildup has occurred in the fuel rod or, if the rod is leaking, that no significant pressure is present.

The leak detector probe of the present invention permits rapid activation of the diaphragm by electromagnetic coils and measurement of the vibrations produced by acoustic transducers mounted within the probe as described in detail below.

BRIEF DESCRIPTION OF THE DRAWINGS

FIG. 1 is a side elevation view, partly in section, of a fuel rod utilizing the upper end cap assembly of the invention of the referenced application.

FIG. 2 is a cross-sectional view taken at line 2—2 of the fuel element shown in FIG. 1.

FIG. 3 is similar to FIG. 2, but illustrates an alternative embodiment.

FIG. 4 is an assembly view of the leak detector probe according to the invention.

DESCRIPTION OF THE PREFERRED EMBODIMENT

While the invention may be used with a fuel rod of any shape, it is particularly suited to the thin, cylindrical fuel rods normally used in pressurized boiling water reactors. As seen in FIG. 1, the fuel pin 101 comprises a thin tube 102 which houses the nuclear fuel pellets 103. Inside the tube 102 the pellets 103 are separated from the lower end cap 104 and the upper end cap 105 by insulating discs 106 and 107, respectively. The pellets 103 are held in position by a spring 108 located in plenum chamber 109 formed between disc 107 and upper end cap 105. More particularly, spring 108 is upwardly restrained by upper end cap 105 which is welded to the upper end of fuel rod 101. The spring 108 pushes down on disc 107 and pellets 103, holding them against disc 106 and lower end cap 104 which is welded to the lower end of fuel rod 101.

During operation of the reactor, fuel pellets 103 produce fission product gases as they emit neutrons and generate heat. These gases accumulate in plenum chamber 109, resulting in a pressure buildup which can exceed 2500 psig after a long period of operation. This pressure, in combination with the temperature and physical stresses placed on fuel pin 101, may result in small cracks within tube 102. If this occurs, the highly radioactive fission product gases may escape from the fuel rod and enter into the reactor core cooling system. To detect leakage of these gases the radioactivity level of the reactor core coolant is constantly monitored. If the level exceeds a predetermined limit, the reactor core is inspected to determine which fuel rods are leaking. The upper end cap assembly of this invention greatly simplifies locating a leaking fuel rod.

As seen in FIG. 2, in a preferred embodiment, the upper end cap assembly comprises an upper end cap 105, a flexible diaphragm 113 and a disc 114 having bleed holes 115. The upper end cap is designed so that its shoulder section 105A fits snugly into tube 102 to seal the upper portion of the fuel element, being attached by welds 110. Shoulder section 105A is provided with a concave bottom surface 105A' which faces toward plenum chamber 109. Within shoulder section 105A and extending into shank section 105B of end cap 105 is an axial cavity 116. The axial cavity is preferably cylindrical and centered in the end cap and of larger diameter and length than required to contain rod 117.

The resilient metal diaphragm 113 is preferably attached to end cap 105 where the concave surface 105A' meets the tube wall 102. It is attached so that cavity 118 is formed which opens up into axial cavity 116, but which is sealed from plenum chamber 109.

Directly below diaphragm 113, disc 114 is suitably attached to tube 102, e.g., by welding under vacuum. In the embodiment of FIG. 2 the diaphragm 113 and disc 114 are positioned so that the diaphragm 113 will lie flat on the upper surface 114A of the disc when it is not being flexed. Disc 114 is provided with at least one bleed hole 115 which extends through the disc allowing fission product gases in plenum chamber 109 to contact the lower surface 113A of diaphragm 113.

During reactor operation, the fission product gases build up in the plenum chamber 109 and exert pressure on the diaphragm 113 through bleed holes 115. This pressure causes the diaphragm to flex up into cavity 118 as is shown in FIG. 2. To determine if pressure has built up in the fuel element, the diaphragm is forced into resonant vibration. This may be done in various ways.

In the preferred embodiment, rod 117 is lifted by an electromagnetic field and then dropped against the diaphragm when the electromagnetic field is switched off. The rod strikes the resilient surface 113B of the diaphragm and sets up resonant vibrations. These vibrations are then damped by energy transfer from the rod to the diaphragm and also to the disc if the diaphragm is in contact with it. The vibration amplitude and rate of dampening is dependent upon the resiliency of the diaphragm, which in turn depends upon the pressure in the fuel element and also upon whether the diaphragm is contacting either disc 114 or the concave surface 105A.

If there is leakage in the fuel element, the pressure will be quite low. This results in very little flexing of the diaphragm. Thus, when the rod strikes the upper surface of the diaphragm, it contacts a "hard" elastic system since the downward motion of the diaphragm is restricted by the disc. In this case, the kinetic energy of the rod is quickly dissipated with only a few bounces.

If there is substantial pressure built up in the fuel rod, as there ordinarily would be after a period of operation, then the rod will strike the diaphragm when it is not restricted by the disc. The energy of the rod is not quickly dissipated, and by comparing the vibrational characteristics with those of a rod having no internal pressure, the presence of pressure is readily detected.

Detection of fuel rod leakage may be done either in place in a nuclear reactor or after individual bundles have been removed and replaced for testing. It will be obvious to one skilled in the art that the shutdown of a nuclear reactor is a relatively complicated and time-consuming procedure. Thus, in order to expedite the testing for leaking fuel rods it may be desirable to attempt to test the fuel bundles in place. This, however, does require the removal of the end plates, which substantially cover the end cap which must be contacted in order to make the desired measurement. Since this procedure of removing the end plates will be more or less difficult, it may be preferable in order to reduce the overall time required to remove suspected bundles and replace them with known good ones in order to place the reactor back on-stream as soon as possible. The testing of the suspected bundles can then be done with more care and less concern for elapsed time when done outside the reactor itself. Nonetheless, in either case the end plate will ordinarily be removed in order to permit access to the fuel rods. Several improved testing devices have been developed which will assist in easy removal of the end plates by remote control. For purposes of the following discussion, it will be assumed that the end plate has been removed, permitting access to the end cap for testing of the individual rods.

A tool or probe 120 as shown in FIG. 4 is placed over the end of each fuel rod in turn. The probe comprises a tubular body 121 which is adapted to fit over the end cap of a fuel rod and thereby place electromagnetic coils 122 contained within the probe 120 adjacent the axial cavity 118 in which the steel rod 117 rests. Also, the extended sleeve portion 121a of the body provides proper alignment of the transducer with the end cap. When the electromagnetic coils 122 are activated, the rod 117 tends to position itself within the magnetic coil 122 and thereby lifts it away from contact with the diaphragm 113. When the electromagnetic coil 122 is switched off, then the rod 117 will drop under the force of gravity to contact the diaphragm 113 and induce vibrations which can be measured.

The measurements are made by a piezoelectric transducer 123 which is bonded, preferably by epoxy cement, into a recess in plug 124 positioned within the tube 121 and above the electromagnetic coils 122 in such a position as to contact the end of the end cap when the probe is properly positioned over the fuel rod. The plug 124, which is preferably made of polyethylene to provide a resilient support for acoustic isolation of the transducer 123, is mounted to be slidably movable within tube 121 and is subjected to spring loading by spring 125 in order to assure firm contact of the transducer 123 with the end cap. It has been found that the transducer, which is typically in the form of a flat disc, should be mounted so as to contact the end cap normal to its axis. Further, the spring force is important in making good contact with the end cap — at least 5 pounds force is needed to provide repeatable results. Leads 126 from the transducer 123 are passed outwardly from the probe 120 to an amplifier and an oscilloscope (not shown) which permit photographing and recording the vibrations which are detected. A typical transducer for this service will be sensitive in the range of 1 KHZ to 200 KHZ, and its resonant frequency is well above the expected vibrations which are to be measured, typically about 625 KHZ, although a range of 500 to 1000 KHZ can be used. The process of positioning the probe over the fuel rod, activating the magnetic coil, deactivating the coil, and measuring the vibrations can be carried out within the space of approximately 2 minutes.

Although in the preferred embodiment, the probe just described would be used to test individual rods, it is within the scope of the invention to use a probe designed according to the same principles to test a plurality of fuel rods simultaneously. Also, fuel rods could be constructed to contain means for activating the vibrating assembly so that only detection facilities need be located in the probe body.

FIG. 3 illustrates another arrangement of the end cap, substantially the same as that illustrated in FIGS. 2 and 4, with the exception that the diaphragm 113 does not rest directly upon the disc when pressure inside the fuel rod is zero. Instead, it is positioned above the disc 114 by a spacer ring 127 which prevents the disc 114 from contacting the diaphragm 113. As would be expected, the vibrational characteristics of the diaphragm 113 are substantially different when using the embodiment of FIG. 4, and, accordingly, although the same measuring technique is used, it has been found necessary to utilize a substantially higher frequency range in order to detect changes in pressure within the fuel rod.

The characteristic performance of the two embodiments are illustrated and discussed in the copending referenced application.

The foregoing description of the preferred embodiments is for illustration of the invention only and should not limit the scope of the invention which is defined by the claims which follow.

What is claimed is:

1. A probe for sensing the vibrational frequencies of a nuclear fuel rod end cap having flexible diaphragm means secured to the interior surface thereof to form a cavity on one side of said diaphragm means isolated from the nuclear fuel and vibration inducing rod means disposed to move freely within said cavity, said probe comprising:
   a. a tubular body member adapted to fit over said end cap;
   b. electromagnetic coil means disposed within said tubular body adjacent a first end thereof so as to be adjacent said vibration inducing rod means when said body member is positioned over said end cap for raising said vibration inducing rod means from a lowered position in contact with said diaphragm means when said coil means is energized and permitting said vibration inducing rod means to drop onto said diaphragm means when said coil means is de-energized, thereby producing vibrations of said diaphragm means; and
   c. transducer means disposed within said body member for contact with said end cap when said body member is positioned over said end cap to sense said vibrational frequencies and to provide electrical output signals in response to the vibrations of said diaphragm means in said end cap.

2. The probe of claim 1 wherein said transducer means is slidably mounted within said body member.

3. The probe of claim 2 including spring means disposed within said body on a first side of said transducer means for pressing said transducer means firmly against said end cap when said body member is in position over said end cap.

4. The probe of claim 3 wherein said spring means is a helical spring having a fully compressed force of more than 5 pounds.

5. The probe of claim 1 wherein said transducer means comprises a flat disc shaped member mounted to contact said end cap normal to its axis when said body member is in position over said end cap.

6. The probe of claim 1 wherein said transducer means is a piezoelectric crystal.

7. The probe of claim 1 wherein the transducer means is mounted on a resilient support member.

8. The probe of claim 1 wherein said transducer means is a piezoelectric crystal cemented by epoxy cement into a recess formed in a polyethylene plug.

9. The probe of claim 1 wherein said body member has a sleeve portion extending beyond said coil means at said first end for aligning said body member with said end cap.

10. The probe of claim 1 including a first elongated channel within said body member for receiving said end cap, said electromagnetic coil means surrounding said elongated channel, said channel opening into a second cavity within said body which is larger than said channel, and said transducer means being mounted in said second cavity adjacent said channel such that said end cap will pass through said channel and contact said transducer when said body member is in position over said end cap.

11. A probe for use in detecting the vibrational characteristics of a vibrating member in a pressurized system in order to determine any leakage in said system as a function of said vibrational characteristics comprising:
   a. a tubular body member having a first substantially closed end and a second end, said second end including an elongated channel extending from said second end toward said first end and opening into a second enlarged cavity which is adjacent said first end;
   b. transducer means located in said second cavity facing said channel;
   c. means for resiliently mounting said transducer means in said second cavity;
   d. said tubular body including sleeve means at said second end extending beyond said channel in a direction away from said first end; and
   e. electromagnetic coil means mounted in said body member surrounding said elongated channel.

12. The combination of a nuclear fuel rod and a probe for sensing the vibrational characteristics of flexible diaphragm means in an end cap for said nuclear fuel rod, said flexible diaphragm means arranged to form a cavity in said end cap on one side of said flexible diaphragm means isolated from the nuclear fuel in said nuclear fuel rod and vibration inducing means having a normal lowered position in contact with said diaphragm means and disposed for free movement within said cavity comprising:

a. a tubular body member positioned over said end cap;
b. transducer means disposed within said body member in operable contact with said end cap for sensing said vibrational characteristics; and
c. electromagnetic coil means surrounding said vibration inducing means and in operable association with said transducer means for causing said vibration inducing means to be raised into said cavity from said normal lowered position upon energization of said electromagnetic coil means and said vibration inducing means causing said diaphragm to vibrate when said electromagnetic coil means is de-energized and thereby permits said vibration inducing means to drop into contact with said diaphragm means, whereby the vibrational characteristics of said diaphragm means is a function of the pressure in said nuclear fuel rod on the side opposite from said cavity.

13. The combination of claim 12 wherein said electromagnetic coil means is operably mounted within said tubular body member.

14. The combination of claim 12 wherein said end cap comprises an elongated shank portion which includes at least a portion of said cavity with said vibration inducing means rod disposed therein for free movement, and said tubular body member includes an elongated channel having said end cap shank portion disposed therein such that said electromagnetic coil means surrounds said shank portion.

15. The combination of claim 14 wherein said transducer means is in direct contact with the free end of said shank portion of said end cap.

16. The combination of claim 14 wherein said tubular body member includes a sleeve extending away from said elongated channel for aligning said probe with said end cap.

* * * * *